United States Patent [19]
Pless et al.

[11] Patent Number: 5,620,477
[45] Date of Patent: Apr. 15, 1997

[54] PULSE GENERATOR WITH CASE THAT CAN BE ACTIVE OR INACTIVE

[75] Inventors: Benjamin D. Pless, Atherton; Steven M. Mitchell, Palo Alto; M. Elizabeth Bush, Fremont, all of Calif.

[73] Assignee: Ventritex, Inc., Sunnyvale, Calif.

[21] Appl. No.: 455,824

[22] Filed: May 31, 1995

Related U.S. Application Data

[63] Continuation-in-part of Ser. No. 221,811, Mar. 31, 1994, abandoned.

[51] Int. Cl.⁶ .................................................. A61N 1/375
[52] U.S. Cl. ........................................................ 607/37
[58] Field of Search .................................. 607/5, 36, 37

[56] References Cited

U.S. PATENT DOCUMENTS

| | | | |
|---|---|---|---|
| 3,760,332 | 9/1973 | Berkovits et al. | 607/37 |
| 4,157,720 | 6/1979 | Greatbatch . | |
| 4,558,702 | 12/1985 | Barreras et al. . | |
| 4,583,543 | 4/1986 | Peers-Trevarton | 607/37 |
| 4,727,877 | 3/1988 | Kallok . | |
| 4,825,871 | 5/1989 | Cansell . | |
| 4,898,173 | 2/1990 | Daglow et al. . | |
| 4,907,592 | 3/1990 | Harper . | |
| 4,922,927 | 5/1990 | Fine et al. . | |
| 5,076,270 | 12/1991 | Stutz, Jr. | 607/37 |
| 5,133,353 | 7/1992 | Hauser . | |
| 5,261,400 | 11/1993 | Bardy . | |
| 5,374,279 | 12/1994 | Duffin, Jr. et al. | 607/5 |

OTHER PUBLICATIONS

"Low–Energy Endocardial Defibrillation using an Axiallary or a Pectoral Thoracic Electrode Location", Saksena, et al., Circulation, vol. 88, No. 6, Dec. 1993, pp. 2655–2660.

"Cardiac Pacemakers—Part 3: Low–Profile Connectors (IS–1) for Implantable Pacemakers", ISO 5841–3, First Edition, 1992–12–01.

"Cardiac Defibrillators—Connector Assembly for Implantable Deifbrillators—Dimensional and Test Requirements", ISO 11318:1993(E).

*Primary Examiner*—William E. Kamm
*Assistant Examiner*—Scott M. Getzow
*Attorney, Agent, or Firm*—Steven M. Mitchell; M. Elizabeth Bush; Mark J. Meltzer

[57] ABSTRACT

A pulse generator having a housing for enclosing and containing pulse generator defibrillation circuitry, particularly adapted to allow for ease of manufacture and use, is disclosed. At least one surface of the housing is electrically conductive and connected to the pulse generator circuitry for delivering defibrillating energy to the heart. The defibrillator is provided with a case activating lead connector cavity having two connector blocks. By plugging in a lead with a pin long enough to contact the only first connector block, the lead becomes active. Using a plug with a longer pin to contact both blocks activates the can. To use neither a lead in the case activating port, nor an active can, a plug with a short or nonconductive pin may be used to plug the cavity without activating the can. By using this system, various electrode configurations can be used as required to provide the optimum system for a given patient. The pulse generator housing is preferably implanted in the left pectoral region proximate the heart with the conductive surface facing the heart. Other implantable electrodes are discharged against the pulse generator housing electrode.

12 Claims, 6 Drawing Sheets

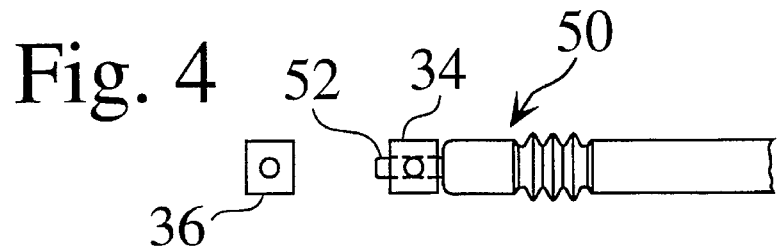
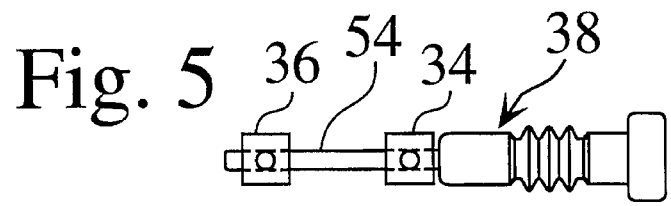
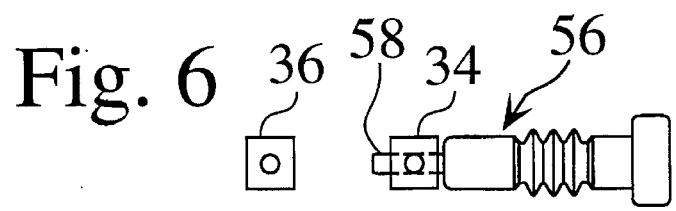
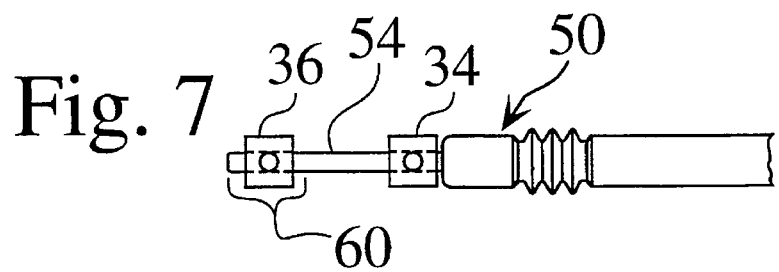
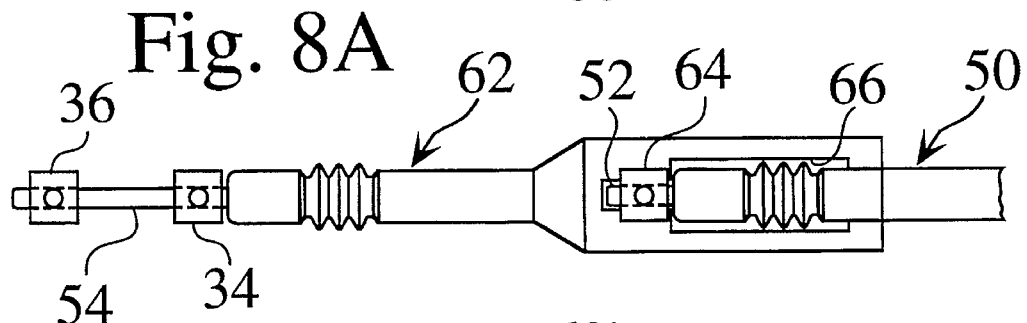
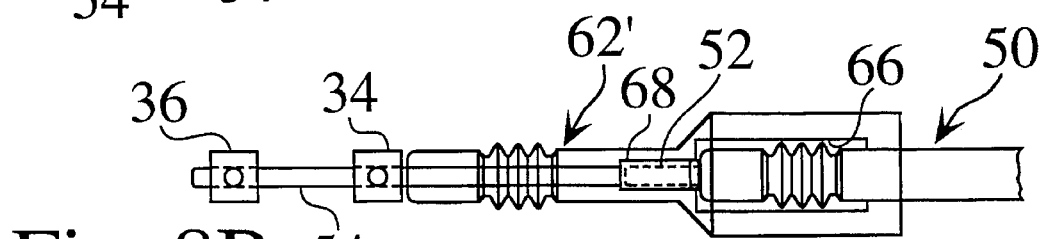

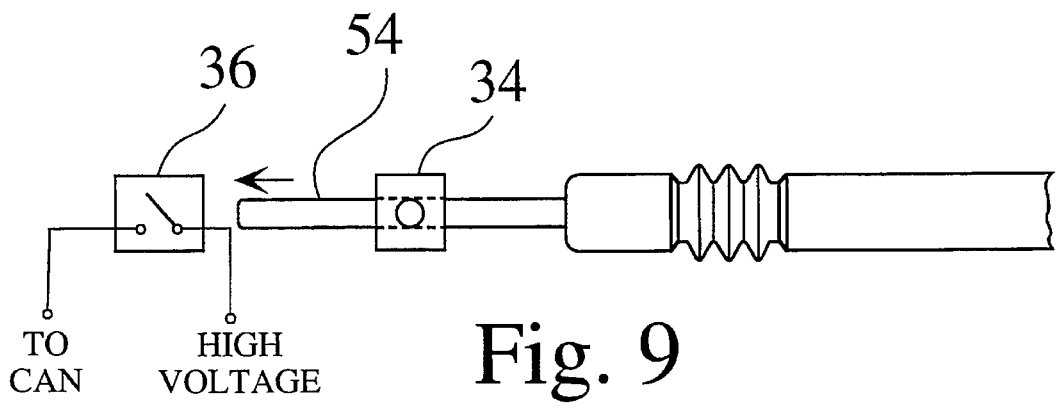
TO CAN    HIGH VOLTAGE
Fig. 9
Fig. 10A
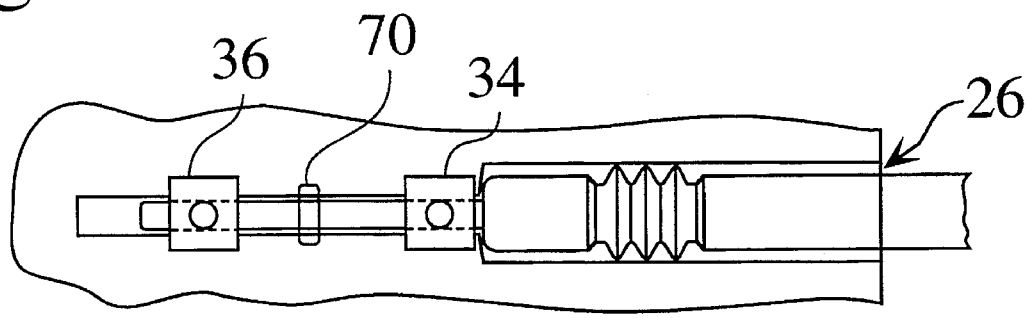
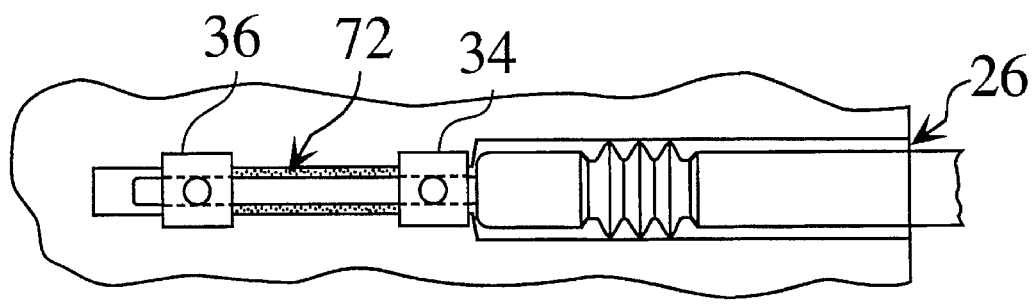
Fig. 10B

PULSE GENERATOR WITH CASE THAT CAN BE ACTIVE OR INACTIVE

This is a continuation-in-part of application Ser. No. 08/221,811, filed on Mar. 31, 1994, now abandoned.

FIELD OF THE INVENTION

The present invention relates generally to implantable cardiac stimulation devices, and more specifically to a defibrillation pulse generator with a case that is either activated or left inactive at the time of implant.

BACKGROUND OF THE INVENTION

There has been substantial work directed towards development of implantable defibrillation systems that avoid the necessity of a thoracotomy. Systems that deliver a defibrillation pulse between one or more endocardial electrodes and an active defibrillator housing are disclosed in U.S. Pat. No. 4,727,877 issued to Kallok; U.S. Pat. No. 4,922,927 to Fine et al.; U.S. Pat. No. 5,133,353 to Hauser; and U.S. Pat. No. 5,261,400 to Bardy, all of which are incorporated herein by reference. As used herein, the words "housing", "enclosure", "case", and "can" are synonymous.

If a device is chosen to have an active can and is placed pectorally, it is unlikely that this decision would be changed in the future. If a lead is used subcutaneously and the inactive can implanted abdominally, it is again unlikely that there would be reason to change this, to "activate the can". Even if this decision were reversed, a surgical procedure would likely be required to reposition the can for effective use as an electrode. Therefore, external programmability of this choice of active or inactive can is not needed, allowing the device to be made simple to manufacture and simple to use.

SUMMARY OF THE INVENTION

The present invention is directed toward the provision of a defibrillator that delivers a defibrillation pulse either between at least one transvenous electrode and at least a portion of the metal enclosure of the defibrillator, or between at least one transvenous electrode and an additional implanted lead located either transvenously, epicardially, or subcutaneously. The decision to use either the pulse generator case or an additional lead, that is, whether the defibrillator can is electrically active or passive, is made by the implanting surgeon at the time of implant.

The defibrillator of the present invention is provided with a case activating lead connector cavity having two connector blocks. By plugging in a lead with a pin which is only long enough to contact the first connector block but not the second, the lead becomes active. Using a plug with a longer pin to contact both blocks activates the can. In the case when neither a lead nor an active can is desired, a plug with a short or nonconductive pin may be used to plug the cavity without activating the can.

By using the present invention, various electrode configurations can be used as required to provide the optimum system for a given patient without having to bring two defibrillators into the operating room, one having an active can and one having an inactive can, and without requiring any programmability from the manufacturer or programming by the physician.

It is thus a primary object of this invention to provide an implantable cardiac stimulation system having defibrillation capabilities with a selectable electrode configuration.

It is an additional object of this invention to provide an implantable cardiac stimulation system that is simpler to implant than prior art systems.

It is a further object of this invention to provide an implantable cardiac stimulation system that can be used with previously implanted defibrillation leads.

It is yet a further object of this invention to provide an implantable cardiac stimulation system that is safer to manufacture and safer to implant.

BRIEF DESCRIPTION OF THE DRAWINGS

The various features and advantages of the present invention may be more readily understood with reference to the following detailed description taken in conjunction with the accompanying drawings in which:

FIG. 4 shows the connector blocks of the case activating connector cavity of FIG. 1, with a lead inserted;

FIG. 5 shows the connector blocks of the case activating connector cavity of FIG. 1, with a can-activating plug inserted;

FIG. 6 shows the connector blocks of the case activating connector cavity of FIG. 1, having a plug to fill the cavity but not activate the can;

FIG. 7 shows the connector blocks of the case activating connector cavity of FIG. 1, having a lead inserted which has a long pin to activate the can; and FIGS. 8A and 8B show the connector blocks of the case activating connector cavity of FIG. 1, having a case activating adapter plug which activates the can and electrically connects a lead to the case activating connector cavity;

FIG. 9 illustrates an alternative embodiment of the invention;

FIGS. 10A and 10B illustrate seals separating the connector blocks of the case activating connector cavity;

FIG. 13 illustrates an embodiment having two case-activating cavities.

DETAILED DESCRIPTION OF THE INVENTION

The decision to use either the pulse generator case or an additional lead, that is, whether the defibrillator can is electrically active or passive, is made by the implanting surgeon at the time of implant. The following are two examples of the many possible sequences of events in the decision making process:

EXAMPLE 1 a.) The defibrillation threshold (DFT) is found to be too high using only two electrodes, with a right ventricular (RV) electrode negative (−) and a superior vena cava (SVC) electrode positive (+).

b.) Various attempts are made to lower the DFT, such as repositioning the SVC electrode, reversing polarity, and changing pulse width. The DFT is still too high.

c.) A subcutaneous (SQ) electrode is desired for location on the left chest wall. However, it is determined that the patient is too thin in the pectoral region for the pulse generator to be implanted there, and thus its housing cannot be used as an electrode.

d.) A separate SQ electrode is implanted in the desired location. The DFT is found to be acceptable using RV−, SVC+, and SQ+.

e.) The pulse generator with an inactive can is implanted in the abdominal region.

EXAMPLE 2 a.) The DFT is found to be too high using RV− and SVC+.

b.) The pulse generator housing is used as a SQ+ electrode in a midaxillary position, with RV− and SVC+. The DFT is still too high.

c.) Attempts are made to lower the DFT by repositioning the SQ pulse generator housing, such as by moving it more anterior or posterior. The DFT is still too high.

d.) The polarity is changed to make RV+, SVC−, and SQ−. The DFT is acceptable.

Figure 1:
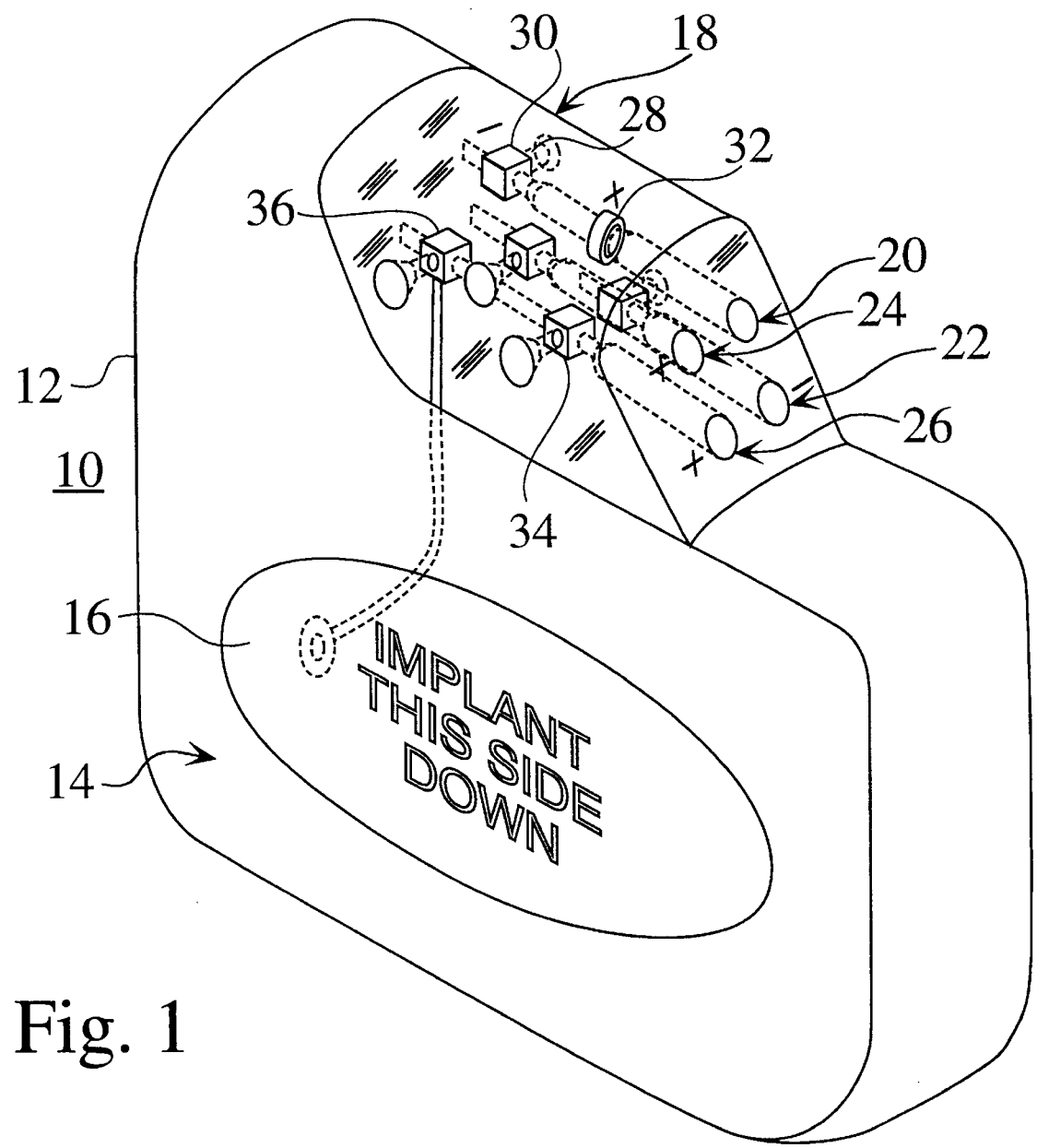
FIG. 1 illustrates the implantable defibrillator according to the present invention.

FIG. 1 illustrates an implantable defibrillator or pulse generator 10 according to the present invention. The defibrillator may have bradycardia and tachycardia pacing capabilities as well as cardioversion and defibrillation capabilities. The housing 12 of the pulse generator 10 is typically titanium, although other corrosion resistant metals may be used. It is partially insulated by a polymeric coating 14, and has an exposed, conductive portion 16 which may serve as an electrode. The polymeric insulating coating 14 serves to keep current flow between electrodes focused toward the heart during a defibrillation shock, so as to lower defibrillation thresholds and to avoid unwanted skeletal muscle stimulation. Alternatively, the entire housing outer surface may be left uncoated, and therefore conductive. The outer surface of the pulse generator may be of a special configuration to facilitate its discharge capabilities. Alternative means for insulating the can may be used, such as an insulative biocompatible boot having a cutout.

A header 18, which is preferably made of transparent or translucent polymeric material, such as epoxy or silicone rubber, contains four lead connector cavities 20, 22, 24, and 26. Alternatively, the header 18 may be built into the housing 12, or may be made of an opaque material; however, the cavities would not be visible. The connector cavities shown are a bipolar pacing lead connector cavity 20, and three unipolar defibrillator connector cavities, two being of the standard type known in the art, and one of a special, case activating type which will be described in detail below.

The pacing lead connector cavity 20 has set screw threads 28 to a connector block 30 for making a mechanical and electrical connection to a pacing lead connector pin, and a garter spring 32 for making an electrical connection to a pacing lead connector ring. Alternatively, other connector mechanisms may be used to electrically and mechanically connect the pin and ring to the pulse generator, such as a set screw connection instead of the garter spring, or the "Collet Grip Connector Block" described in U.S. Pat. No. 5,489,225 to Chris Julian, which is assigned to the assignee of the present application and is incorporated herein by reference. The pacing pin electrical connection 30 is negative in polarity, and the ring connection 32 is positive. The pacing lead connector cavity 20 may be of the IS-1 BI type described in ISO 5841-3:1992(E) "Cardiac pacemakers—Part 3: Low-profile connectors (IS-1) for implantable pacemakers" (International Standard). Alternatively, the header may include a pair of pacing lead cavities for use with two unipolar leads, or for one bipolar bifurcated lead, or other configurations, as are well known in the art.

The standard defibrillation lead connector cavities 22 and 24 are of opposite polarity, and are designed for high energy defibrillation pulses. They may be of the DF-1 type described in ISO 11318:1993(E) "Cardiac defibrillators—Connector assembly for implantable defibrillators—Dimensional and test requirements" (International Standard). Again, block and set screw connections are shown in most of the figures, but any suitable connection mechanism known in the art may be used for the terminals such as a garter spring shown as contact 78 in FIG. 12.

The case activating defibrillation connector cavity 26 has first and second contacts, or connector blocks 34 and 36. Other electrical connection mechanisms could alternatively be used. The first connector block 34 is coupled to a positive terminal of the pulse generator circuitry (not shown). The second connector block 36 is electrically coupled to the conductive portion 16 of the defibrillator case 12. Plugging in a lead connector with a pin only long enough to contact the first connector block 34 but not the second connector block 36, as shown in FIG. 4, will activate the electrode attached to the lead connector, making it positive during a defibrillation shock. Using a plug with a longer pin to contact both blocks 34 and 36, as shown in FIG. 5, will activate the device housing, making it positive during a shock. To use neither a lead in the case activating port, nor an active can, a plug with a short or nonconductive pin may be used to plug the cavity without activating the can, as shown in FIG. 6.

By using the system of the present invention, various electrode configurations can be used as required to provide the optimum system for a given patient without having to bring two defibrillators into the operating room, one active and one inactive, and without requiring any programmability from the manufacturer or programming by the physician.

Another advantage provided by the defibrillator of the present invention is realized both during manufacture and during handling by implanting medical personnel. In a system having a permanently active can, or one that can be conventionally programmed to be active or inactive, there is the danger that the pulse generator could deliver a high voltage shock to anyone handling the device during manufacture or implant, because it is impossible to tell by visual inspection whether such a system is turned on, thus requiring interrogation using a programmer or similar method. On the other hand, the defibrillator of the present invention is not active unless a case-activating plug or lead is inserted in the case activating cavity as can be easily noted by visual inspection. Simply by not inserting this plug, the defibrillator remains inactive throughout the manufacturing process. During implant, the plug need not be inserted until near the end of the implant procedure. Once the plug is inserted, it is clearly visible, and the defibrillator should be handled accordingly.

It is noted that FIG. 1 shows only one case activating connector cavity 26, having positive polarity, which has been found to be the most effective polarity for the active can. However, the negative lead connector cavity 22 may also be of this case activating type having a longer pin cavity and a second connector block. This would provide the implanting physician with yet another option in electrode configuration choice.

Other options for connector cavity configuration within the header are possible. For example, the header may be made smaller by providing only two defibrillator connector cavities instead of three, with at least one of the two being of the case activating type described. The device may alternatively, but not preferably, be made without pacing capabilities, thereby eliminating the pacing lead connector cavity.

Figure 2:
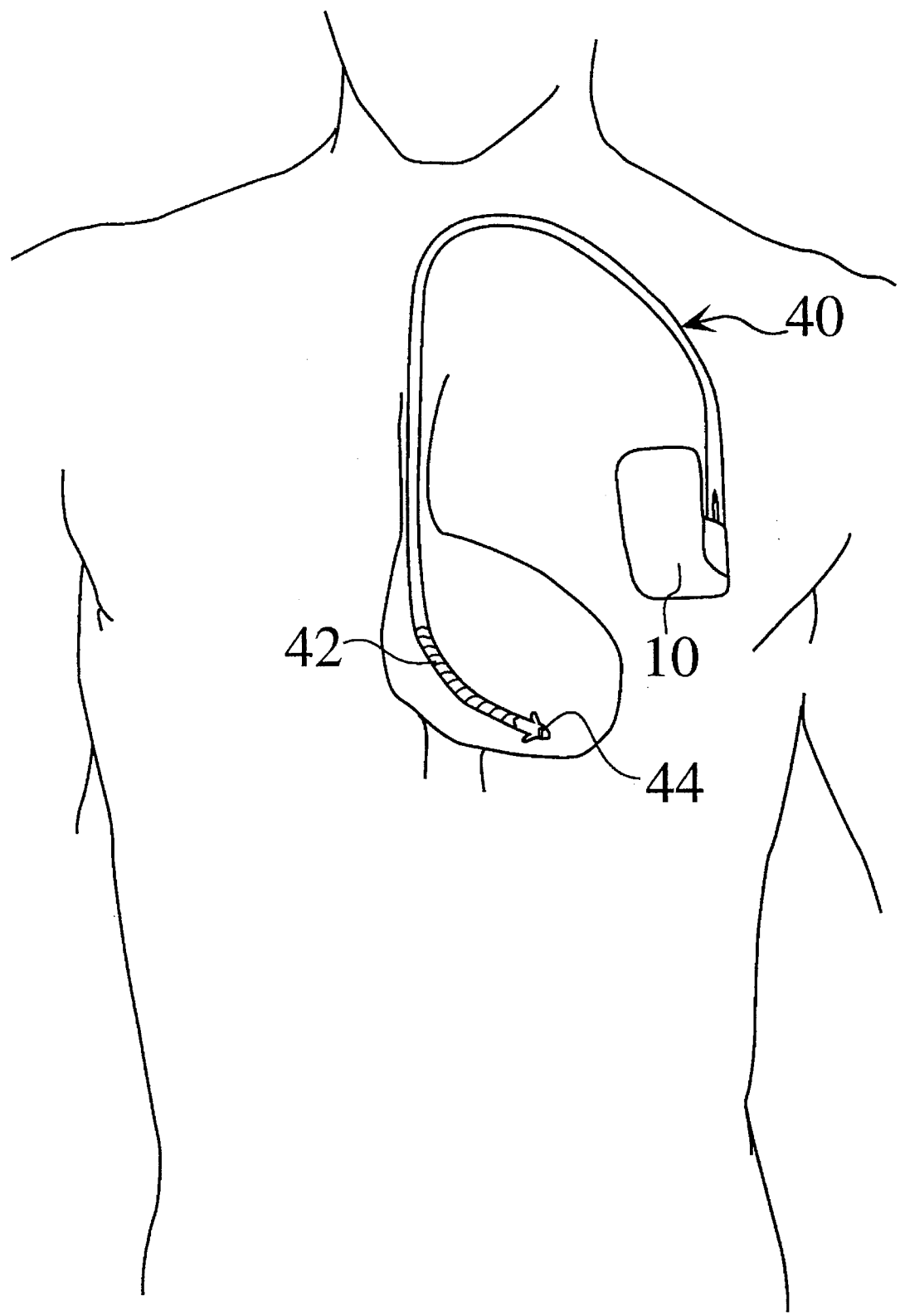
FIG. 2 illustrates the placement of an activated pulse generator of the present invention in the patient's pectoral region adjacent the heart, connected to an implanted transvenous lead.

FIG. 2 illustrates the placement of the pulse generator 10 near the heart in the pectoral region of the patient. It is connected to an implanted transvenous lead 40, which has one high surface area electrode 42 which is used alternately for defibrillation and for sensing, and a pacing tip electrode 44. The electrodes are located in the right ventricle and the defibrillator generator is located in the left pectoral region of the chest. Alternatively, the generator may be located at the level of the ventricles or in the abdominal region. The positive defibrillation lead connector cavity 24 (not shown) is plugged to prevent body fluids from entering it, using a plug similar to the one shown in FIG. 6. Alternatively, an electrode may be connected to this connector cavity.

It should also be noted that a defibrillator of the present invention may be used with preexisting leads. For example, if during a typical defibrillator replacement, due to end of battery life, the DFT is found to have increased in a patient having only RV and SVC electrodes, a replacement defibrillator with an active can as an additional electrode may be used with the existing leads to decrease the DFT.

Figure 3:
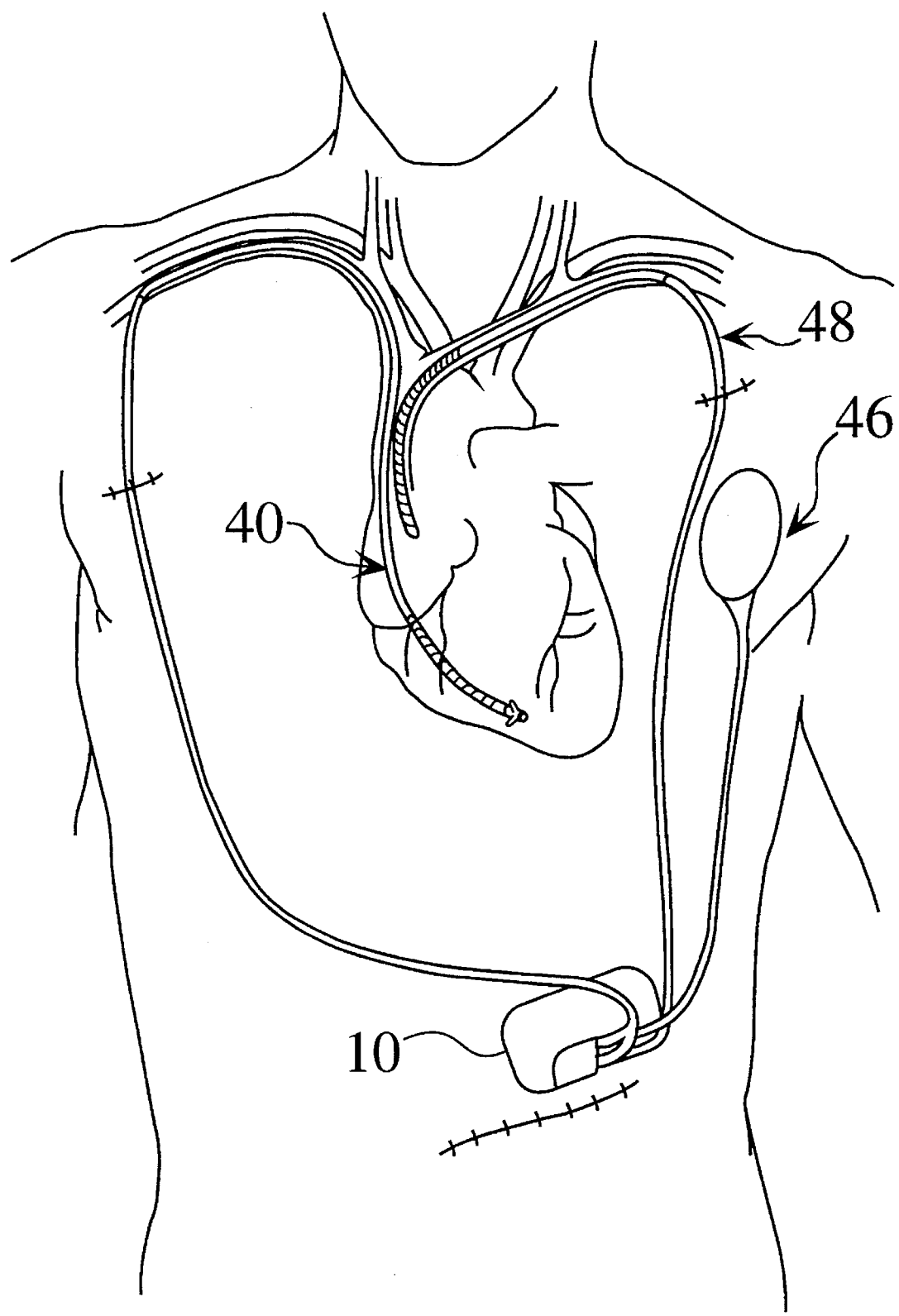
FIG. 3 illustrates the placement of an inactive pulse generator case of the present invention in the abdominal region, having a subcutaneous lead implanted in the case activating connector cavity, and also connected to a right ventricular and a superior vena cava lead.

FIG. 3 illustrates the placement of the inactive pulse generator case in the abdominal region, having a subcutaneous lead 46 implanted in the left chest wall and connected to the case activating connector cavity. Pulse generator 10 is also connected to a right ventricular lead 40 and a superior vena cava lead 48.

FIG. 4 shows the connector blocks 34 and 36 of the case activating connector cavity 26 of FIG. 1, with a lead connector 50 inserted. Lead connector 50 includes a lead connector pin 52, which is too short to contact the second connector block 36. Thus, only the electrode attached to the lead connector pin 52 is active for defibrillation; the defibrillator case remains inactive.

FIG. 5 shows the connector blocks 34 and 36 of the case activating connector cavity 26 of FIG. 1, with a can-activating plug 38 inserted. Plug 38 includes a long pin 54 which contacts both connector blocks 34 and 36 serving to electrically connect the can 12 to the positive defibrillator output of the pulse generator 10.

FIG. 6 shows the connector blocks 34 and 36 of the case activating connector cavity 26 of FIG. 1, having a plug 56 to fill the cavity 26 but not activate the can. The pin 58 is strictly for making a mechanical connection to the cavity, and may be only long enough to contact the first connector block 34 as shown, and/or may be of nonconductive material. This plug 56 prevents body fluids from entering the cavity, which prevents the blocks from being shorted together by the fluid, prevents corrosion of the connector blocks, and keeps the cavity open for optional future use.

FIG. 7 shows the connector blocks 34 and 36 of the case activating connector cavity 26 of FIG. 1, having a lead connector 50 inserted which has a long pin 54 to activate the can. In this embodiment, both the device housing and the electrode attached to the lead connector are of the same polarity. To use this embodiment, the decision to use an active can must be made before the lead is implanted, since the longer lead connector pin 54 is required. Alternatively, a lead with a longer connector pin may be implanted prior to making the decision to use an active or inactive can; then, an insulative covering (not shown) may be placed on the end of the lead connector pin to prevent electrical connection with only the second connector block 36, should the implanting physician choose not to activate the can.

As shown in the figures, both contacts 34 and 36 may be of the same size, and the long connector pin 54 may be of constant diameter over its entire exposed length. Alternatively, to allow room for an insulative cap, sleeve, or other covering, the pin diameter may be smaller on the end 60 where it passes through the second contact 36. See FIG. 11.

FIGS. 8A and 8B show the connector blocks 34 an 36 of the case activating connector cavity 26 of FIG. 1, having a lead adapter 62 which activates the can and electrically attaches a lead connector 50 to the case activating connector cavity. This embodiment allows the use of a "standard" lead connector pin 52 on lead connector 50. FIG. 8A shows lead adapter 62 having a connector block 64 electrically connected to its connector pin 54 by means of a cable or coil (not shown). Adapter 62 includes a cavity 66 and block 64 which accept a "standard" lead connector. The lead adapter pin 54 is sufficiently long to make contact with both connector blocks 34 and 36, thereby activating the conductive portion of the pulse generator case. FIG. 8B shows another embodiment of an adapter 62' which can accept a "standard" lead connector and make contact with both connector blocks 34 and 36 to activate the can. This type of space saving adapter uses a sliding collar 68 to connect and disconnect the lead connector pin 52 and the adapter, and is described in U.S. Pat. No. 5,439,391 entitled "Lead Adapter" to McEtchin et al., which is assigned to the assignee of the present invention and is incorporated herein by reference.

FIG. 9 illustrates an alternative embodiment of the invention, in which the second contact 36 may further include a switch which is triggered by the insertion of a longer pin, such as those shown in FIGS. 5, 7, 8A and 8B. The longer pin need not be conductive for this embodiment, since it is acting only as a mechanical triggering device to activate the defibrillator case. Whereas the embodiment previously described automatically forces the first and second contacts to be the same polarity, this alternative embodiment allows the second contact to be independently connected to the pulse generator circuitry, and therefore may be of the same or different polarity as the first contact.

The sealing mechanisms shown on all of the plugs, lead connectors, and adapters in FIGS. 4 through 8B that are intended to seal against the connector cavities are used to prevent body fluids from entering the cavities. However, in order to prevent fluid intrusion should these seals fail, an additional seal or other provisions may be included between connector blocks 34 and 36 to keep a fluid path from electrically connecting the blocks. As shown in FIG. 10A, the seal may be an elastomeric membrane 70 provided between, and separating, connector blocks 34 and 36, which has a small slit through which a long connector pin may be inserted, but which remains sealed when no pin is inserted and may seal against the connector pin when one is present. Alternatively, the membrane may have no such slit, but may be of such structure that it is easily pierced with a long pin. In the case where connector blocks 34 and 36 are of the same polarity, and the can is activated, no seal is necessary between the connector blocks; in that case, the seal can be of a design that does not reseal once pierced.

As another alternative, the seal may be a viscous, non-conductive silicone grease, silicone gel, or the like 72, as shown in FIG. 10B. The grease or gel is displaced by the pin during pin insertion, but then reforms to block the conductive fluid path between the connector blocks 34 and 36 thereby achieving a fluid insulated connection.

Figure 11:
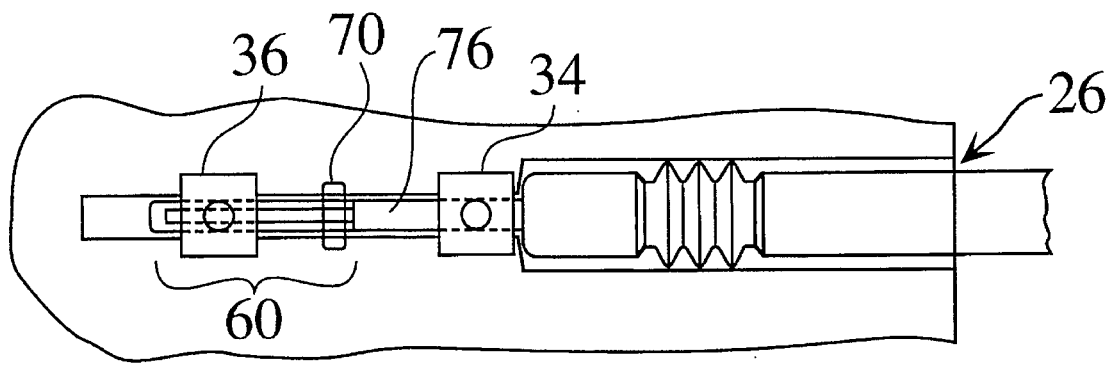
FIG. 11 illustrates an embodiment having an insulative cap, sleeve, or other covering.

FIG. 11 illustrates an embodiment having an insulative cap, sleeve, or other covering 74 over the pin 76 in the region of contact 36. Pin 76 is smaller on the end 60 where it passes through the contact 36.

Figure 12:
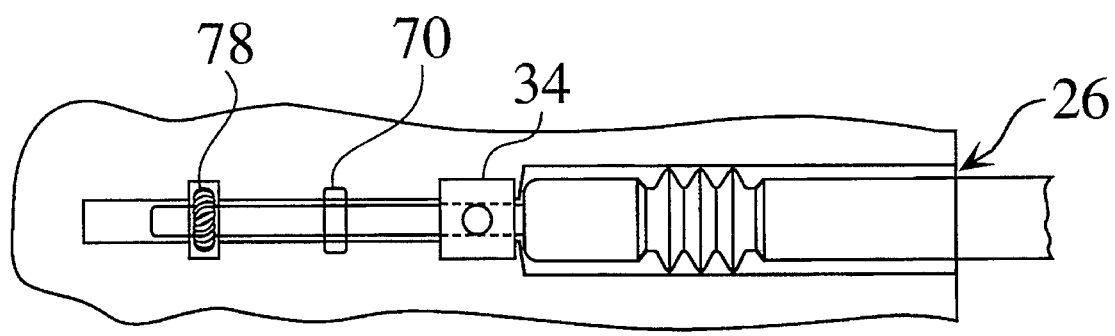
FIG. 12 illustrates an embodiment having a garter spring for the contact electrically connected to the case.

FIG. 12 illustrates an embodiment having a garter spring 78 for the contact electrically connected to the case.

FIG. 13 illustrates an embodiment having two case-activating cavities, 22 and 26.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable cardiac stimulator comprising:

a pulse generator case;

defibrillation pulse generator circuitry housed in said case;

a header attached to said case, said header including at least first and second cavities;

said first cavity having a contact for making an electrical connection; and said second cavity having a first contact for making an electrical connection and a second contact electrically connected to at least a portion of said case, wherein said second contact of said second cavity further includes a switch, said switch being triggerable by insertion of a pin into said second cavity, and wherein triggering said switch activates said at least a portion of said case for use as an electrode.

2. The implantable cardiac stimulator of claim 1 wherein said first contact of said second cavity and said second contact of said second cavity are of opposite polarities.

3. The implantable cardiac stimulator of claim 2, wherein said second cavity further includes a fluid seal between said first and second contacts, and wherein said fluid seal comprises a viscous, nonconductive, fluid-impervious material.

4. An implantable cardiac stimulator comprising:

a pulse generator case;

defibrillation pulse generator circuitry housed in said case;

a header attached to said case, said header including at least first and second cavities;

said first cavity having a contact for making an electrical connection; and said second cavity having a first contact for making an electrical connection and a second contact electrically connected to at least a portion of said case wherein said first cavity further includes a second contact electrically connected to at least a portion of said pulse generator case, and wherein said second contact of said second cavity further includes a switch, said switch being triggerable by insertion of a pin into said second cavity, and wherein triggering said switch activates said at least a portion of said case for use as an electrode.

5. An implantable cardiac stimulator comprising:

a pulse generator case;

defibrillation pulse generator circuitry housed in said case;

a header attached to said case, said header including at least first and second cavities;

said first cavity having a contact for making an electrical connection; and said second cavity having a first contact for making an electrical connection and a second contact electrically connected to at least a portion of said case wherein said first cavity further includes a second contact electrically connected to at least a portion of said pulse generator case, and wherein said second contact of said first cavity further includes a switch, said switch being triggerable by insertion of a pin into said first cavity, and wherein triggering said switch activates said at least a portion of said case for use as an electrode.

6. An implantable cardiac stimulator system comprising:

a pulse generator case;

defibrillation pulse generator circuitry housed in said case;

a header attached to said case, said header including at least first and second cavities;

said first cavity having a contact for making an electrical connection of a first polarity;

said second cavity having a first contact for making an electrical connection of a second polarity and a second contact electrically connected to at least a portion of said case;

a transvenous lead having a first defibrillation lead connector inserted into said first cavity;

a second defibrillation lead connector coupled to a defibrillation electrode and inserted into said second cavity, said second defibrillation lead connector having a pin contacting said second cavity first and second contacts; and an insulating covering installable onto the end of said defibrillation lead connector pin to insulate said pin from said second contact but not from said first contact.

7. The implantable cardiac stimulator system of claim 6 wherein said pin is of a smaller diameter on the end that makes contact with said second contact.

8. The implantable cardiac stimulator system of claim 6 wherein said second contact is larger to accept said pin having said insulating covering.

9. The implantable cardiac stimulator system of claim 6, wherein said insulating covering is removable from the end of said defibrillation lead connector pin following installation of said insulating covering onto said defibrillation lead connector pin.

10. The implantable cardiac stimulator system of claim 6, wherein said second contact of said second cavity further includes a switch, said switch being triggerable by insertion of a pin into said second cavity, and wherein triggering said switch activates said at least a portion of said case for use as an electrode.

11. An implantable cardiac stimulator system comprising:

a pulse generator case;

defibrillation pulse generator circuitry housed in said case;

a header attached to said case, said header including at least first and second cavities;

said first cavity having a contact for making an electrical connection of a first polarity;

said second cavity having a first contact for making an electrical connection of a second polarity and a second contact electrically connected to at least a portion of said case;

a transvenous lead having a defibrillation lead connector inserted into said first cavity; and an adapter inserted into said second cavity, said adapter having a pin contacting said second cavity first and second contact and further including:

an insulative adapter body;

an adapter cavity; and an adapter electrical contact electrically attached to said pin, wherein said adapter electrical contact contacts a defibrillation lead connector pin inserted into said adapter cavity and wherein said adapter pin is longer than said defibrillation lead connector pin.

12. The implantable cardiac stimulator system of claim 11, wherein said second contact of said second cavity further includes a switch, said switch being triggerable by insertion of said adapter pin into said second cavity, and wherein triggering said switch activates said at least a portion of said case for use as an electrode.

* * * * *